United States Patent
Swartling et al.

(10) Patent No.: US 11,331,512 B2
(45) Date of Patent: May 17, 2022

(54) SYSTEM AND METHOD FOR DETERMINING LIGHT ATTENUATION AT OPTICAL MEMBERS INSERTED IN TISSUE

(71) Applicant: SpectraCure AB, Lund (SE)

(72) Inventors: Johannes Swartling, Lund (SE); Ida Arvidsson, Höör (SE); Johan Axelsson, Lund (SE)

(73) Assignee: SpectraCure AB, Lund (SE)

( * ) Notice: Subject to any disclaimer, the term of this patent is extended or adjusted under 35 U.S.C. 154(b) by 0 days.

(21) Appl. No.: 17/600,302

(22) PCT Filed: Apr. 6, 2020

(86) PCT No.: PCT/EP2020/059790
§ 371 (c)(1),
(2) Date: Sep. 30, 2021

(87) PCT Pub. No.: WO2020/201580
PCT Pub. Date: Oct. 8, 2020

(65) Prior Publication Data
US 2022/0088405 A1    Mar. 24, 2022

(30) Foreign Application Priority Data
Apr. 4, 2019 (EP) .................... 19167324

(51) Int. Cl.
*A61N 5/06* (2006.01)
*A61N 5/067* (2006.01)
*G16H 20/40* (2018.01)

(52) U.S. Cl.
CPC .......... *A61N 5/0601* (2013.01); *A61N 5/062* (2013.01); *A61N 5/067* (2021.08); *A61N 5/0625* (2013.01);
(Continued)

(58) Field of Classification Search
CPC ...... A61N 5/0601; A61N 5/067; A61N 5/062; A61N 5/0625; A61N 2005/0612; A61N 2005/0628; A61N 2005/063; G16H 20/40
See application file for complete search history.

(56) References Cited

U.S. PATENT DOCUMENTS 6,138,046 A    10/2000  Dalton
8,986,358 B2 *  3/2015  Svanberg ............... A61N 5/062
                                               607/88
(Continued)

FOREIGN PATENT DOCUMENTS

EP    1470837 A2     10/2004
WO    2012076631 A1   6/2012
WO    2017015674 A1   1/2017

OTHER PUBLICATIONS

Heping Xu et al: "Determination of the optical properties of tissue-simulating phantoms from interstitial frequency domain measurements of relative fluence and phase difference", Optics Express, vol. 14, No. 14, Jan. 1, 2006 (Jan. 1, 2006), p. 6485, XP055628237, DOI: 10.1364/0E.14.006485.
(Continued)

*Primary Examiner* — Jonathan T Kuo
(74) *Attorney, Agent, or Firm* — Veros Legal Solutions, LLP

(57) ABSTRACT

A system and method for determining or estimating the presence and effect of light-attenuating inhomogeneities in tissue when performing medical treatment or diagnostics using optical members in tissue. The system and method comprising inserting a plurality of optical members into the tissue, and then measuring by emitting light through a sub-set of optical members at a time, while measuring the light collected by another sub-set of optical members. Combining said measurement data with a model for light propagation in tissue, and setting up a system of equations.
(Continued)

Solving the unknown attenuation values from said system of equations.

16 Claims, 5 Drawing Sheets

(52) U.S. Cl.
CPC ....... *G16H 20/40* (2018.01); *A61N 2005/063* (2013.01); *A61N 2005/0612* (2013.01); *A61N 2005/0628* (2013.01)

(56) References Cited

U.S. PATENT DOCUMENTS

| | | | |
|---|---|---|---|
| 2005/0106744 A1* | 5/2005 | Mizushima | G01N 21/3563 436/164 |
| 2006/0095100 A1 | 5/2006 | Lee et al. | |
| 2008/0033339 A1* | 2/2008 | Tulip | A61N 5/0601 604/20 |
| 2011/0034971 A1* | 2/2011 | Svanberg | A61N 5/062 607/88 |

OTHER PUBLICATIONS

International Search Report and Written Opinion dated Jun. 26, 2020 in International Patent Application No. PCT/EP2020/059790.
Julia L. Sandell et al: "A review of in-vivo optical properties of human tissues and its impact on PDT", Journal of Biophotonics, vol. 4, No. 11-12, Oct. 7, 2011 (Oct. 7, 2011), pp. 773-787, XP055451289, DE. ISSN: 1864-063X, DOI: 10.1002/jbio.201100062.

* cited by examiner

SYSTEM AND METHOD FOR DETERMINING LIGHT ATTENUATION AT OPTICAL MEMBERS INSERTED IN TISSUE

BACKGROUND OF THE INVENTION

Field of the Invention

This disclosure pertains in general to determine the presence of light-attenuating inhomogeneities in tissue when performing medical treatment or diagnostics using optical fibres in tissue. More particularly the disclosure relates to determining aggregation of blood at optical fibres which might affect the light propagation from or to said optical fibres. Especially the disclosure relates to determining the light attenuation due to blood aggregation to improve light dose control when performing photodynamic therapy or laser hyperthermia using optical fibres or other optical probes in tissue.

Background of the Disclosure

The disclosure relates to a system and method to improve light dose control when performing light-based therapy using optical fibres or other optical probes in tissue.

Within the field of medical therapy of tumour diseases, several treatment modalities have been developed for treatment of malignant tumour diseases. Surgery, cytostatic treatment, treatment with ionising radiation (gamma or particle radiation), isotope therapy, and brachytherapy employing radioactive needles are examples of common treatment modalities. In spite of great progress within therapy, tumour diseases continue to account for much human suffering, and are responsible for a high percentage of deaths in Western countries. A treatment modality, photodynamic therapy (PDT), provides a complement or alternative in the treatment field. A light-activated agent, normally referred to as a sensitizer, is administered to the body percutaneously, orally or topically. It may accumulate in malignant tumours to a higher extent than in the surrounding healthy tissue. The tumour area is then irradiated with non-thermal red light, normally from a laser, leading to excitation of the sensitizer to a more energetic state. Through energy transfer from the activated sensitizer to the oxygen molecules of the tissue, singlet state oxygen and other oxidative species are formed. Singlet oxygen is known to be particularly toxic to tissue; cells are eradicated and the tissue goes in necrosis. Because of the localization of the sensitizer to tumour cells a unique selectivity is obtained, where surrounding healthy tissue is spared.

Laser hyperthermia is a related treatment modality that, instead of utilising a photosensitizer, heats the target tissue by higher laser power and causes tissue death by thermal effect.

The limited penetration in tissue of the activating red light is a drawback of PDT, and similar limitations are present for laser hyperthermia. The result is that only surface tumours can be treated by surface irradiation. In order to treat thicker and deep-lying tumours, interstitial light delivery can be utilized. Here, light-conducting optical fibres are brought into the tumour using, e.g. a syringe needle, in the lumen of which a fibre has been placed.

In order to achieve an efficient treatment, several fibres may be used to ascertain that all tumour cells are subjected to a sufficient dose of light. It has been shown to be achievable to perform dose calculations of the absorptive and scattering properties of the tissue. E.g., in the patent EP 1 443 855 A1 a system is described, where multiple fibres are used for treatment as well as for measurement of the light flux which reaches a given fibre in the penetration through the tissue from the other fibres. In this way an improved calculation of the correct light dose can be achieved for all parts of the tumour.

A problem when performing interstitial illumination as described in the previous is that blood or other matter may accumulate at the distal ends of the optical fibres, which can attenuate the light exiting the fibres. The consequence of this is twofold: firstly, the attenuation may reduce the intended effect of the treatment since the light dose further away from the fibres is reduced, and secondly, any optical measurements performed through the fibres may be affected by the attenuation of the light.

Hence, new improved apparatus and methods for determining the impact of the presence of blood aggregation at medical optical fibres placed inside tissue would be advantageous.

SUMMARY OF THE INVENTION

Accordingly, examples of the present disclosure preferably seek to mitigate, alleviate or eliminate one or more deficiencies, disadvantages or issues in the art, such as the above-identified, singly or in any combination by providing a device, system or method according to the appended patent claims for determining attenuation of light in tissue. The attenuation may be used for determining the impact of the presence of blood aggregation at medical optical members, such as optical fibres, waveguides, light sources, or photodiodes, placed inside tissue.

When optical members are inserted into tissue, the trauma to the tissue may cause bleeding that accumulates at the tip of the member, or along the length of the member. At visible and infrared wavelengths, the light absorption of blood is typically much higher than the average light absorption of tissue, due to the high concentration of haemoglobin in the blood. The accumulated blood thus acts as a light absorber that attenuates the emission of light from the optical members.

One purpose of the present disclosure is to determine or estimate attenuation of the light in the tissue. Another purpose of the present disclosure is to determine or estimate attenuation of light that is caused by inhomogeneities at medical optical members placed inside tissue, such as accumulation of blood where the light is emitted from the members. Such inhomogeneities may cause local attenuation of the light and which may need to be accounted for. For determining or estimating attenuation of light, the disclosure in general consists of two steps, where the first step is to perform optical measurements to provide data that may be used to deduce the light attenuation. When a plurality of optical members are used, this step consists if emitting light by one member at a time, or by a certain collection of members, and detecting the light that is collected by other members at some distance away from the emitting members.

In the second step, the attenuation is determined by using a model-based algorithm to estimate the attenuation. This attenuation may be used for determining or estimating the attenuation caused by an inhomogeneity, such as the blood accumulation. The determination or estimation is in general performed by solving an inverse problem where the measurement data set from the first step is used as input and a set of attenuation values is the output.

It should be emphasized that the disclosure is not limited to use when performing treatment of malignant tumours, but may be used in any situation where a treatment of tissue using optical members is performed, or any situation where measurements in tissue using optical members is performed.

An advantage of using the described method of determining or estimating the light-attenuation is improved accuracy of the determined or estimated effective attenuation coefficients and attenuation values. The accuracy of the determined or estimated effective attenuation coefficients and attenuation values means that the dosimetry may be improved.

It should also be emphasized that the term "comprises/comprising" when used in this specification is taken to specify the presence of stated features, integers, steps or components but does not preclude the presence or addition of one or more other features, integers, steps, components or groups thereof.

BRIEF DESCRIPTION OF THE DRAWINGS

These and other aspects, features and advantages of which examples of the disclosure are capable of will be apparent and elucidated from the following description of examples of the present disclosure, reference being made to the accompanying drawings, in which.

DESCRIPTION OF EXAMPLES

The following disclosure focuses on examples of the present disclosure applicable to determining or estimating light attenuation in tissue. The disclosure may be applicable for determining the impact of the presence of light-attenuating inhomogeneities at medical optical members, such as optical fibres, waveguides, light sources, and/or photodiodes placed inside tissue. For example, this is advantageous for determining the impact of the presence of blood aggregation at medical optical members placed inside tissue. However, it will be appreciated that the description is not limited to this application but may be applied to many other systems where determining the impact of the presence of light-attenuating inhomogeneities at medical optical members placed inside a turbid medium.

Figure 1:
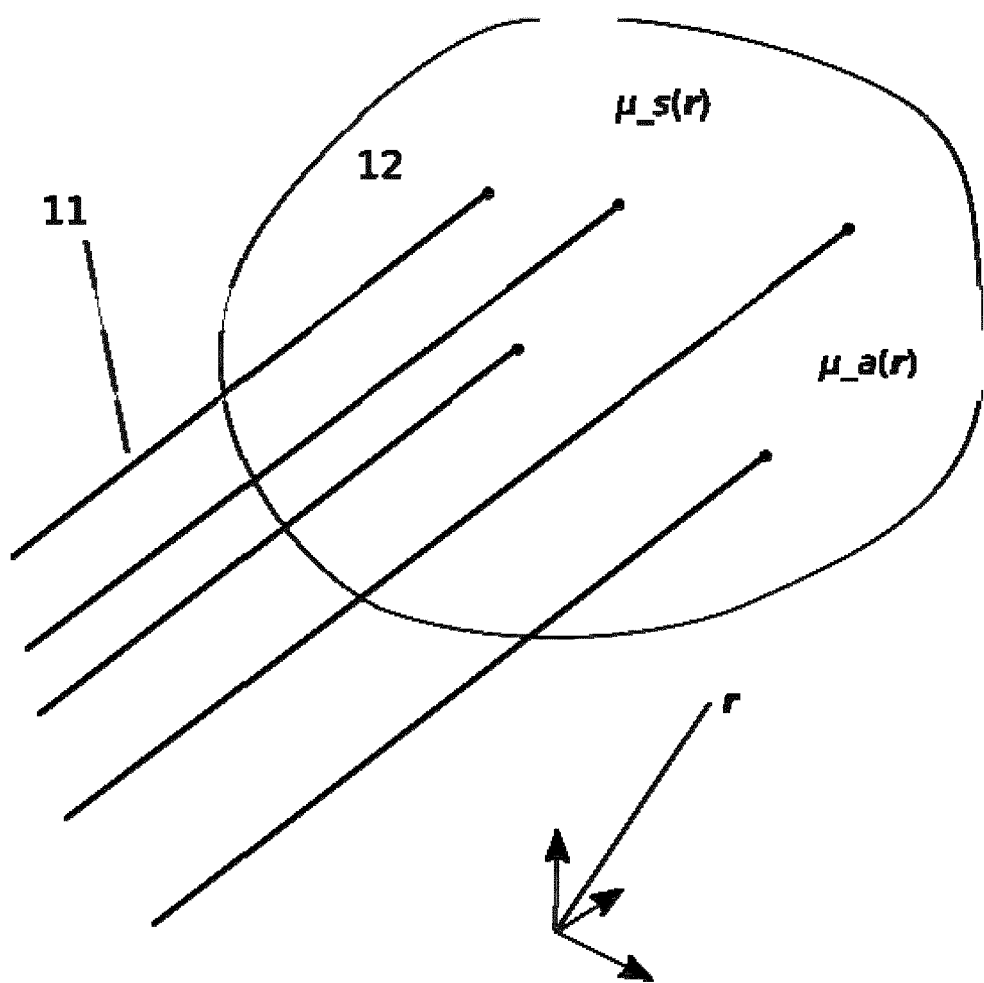
FIG. 1 is illustrating a plurality of optical members (11) that are inserted into a tissue (12), said tissue characterised by having light-scattering properties denoted $\mu_s(r)$ in the geometrical coordinate r, and light-absorbing properties denoted $\mu_a(r)$.

Consider a tissue that has light-scattering and light absorbing properties as illustrated in FIG. 1. A plurality of optical members (11), such as optical fibres, waveguides, light sources, and/or photodiodes is placed inside the tissue (12) for the main purpose of delivering a light dose into the tissue, or to perform measurements of the optical characteristics of the tissue. The light-scattering properties of the tissue may be denoted $\mu_s(r)$ in the geometrical coordinate r. Likewise, the light-absorbing properties are denoted $\mu_a(r)$. The light fluence in any point r in the tissue due to one or multiple light sources may in general for example be described by Boltzmann transport theory for radiative transfer. The transport equation in general requires numerical solution. For the purpose of example, analytical solutions to the transport equation exist in some specific cases. For example, the light fluence rate at distance r from a point source in a homogeneous medium, provided that $\mu_s(r) \gg \mu_a(r)$, may be expressed as $$\phi(r) = (4\pi D r)^{-1} \exp(-\mu_{eff} r) \quad (1)$$

where $\mu_{eff} = [3\mu_a(\mu_a + \mu_s)]^{1/2}$, and $D = [3(\mu_a + \mu_s)]^{-1}$. $\mu_{eff}$ is the effective attenuation coefficient and D is the diffusion coefficient. Hence, the fluence rate as a function of the distance from the light source typically follows some type of exponential, determined by the effective attenuation coefficient $\mu_{eff}$.

If light-attenuating inhomogeneities are present, the absorption may be increase or decrease compared to tissue in general. In case bleeding occurs at the optical members, the accumulated blood will absorb light to a higher degree than the tissue in general, since blood has an inherent high light absorption due to the high concentration of haemoglobin. Assuming that the blood only accumulates locally around the member, it will act to attenuate the light that is emitted from the member (and attenuate the light that is collected by the member in case it is used for measurements). An attenuation value A may be incorporated to the expression for the light fluence rate:

$$\phi(r) = A(4\pi D r)^{-1} \exp(-\mu_{eff} r) \quad (2)$$

where $0 \leq A \leq 1$. Assuming that the entire volume of tissue may be approximated as homogeneous except for the presence of inhomogeneities, such as local bleeding at each member, and that each member is considered a point source, this gives a set of attenuation values $A_i$ for each member, where the index $i = 1 \ldots N$ for N members.

To determine the attenuation values $A_i$, the first step may be to perform a set of measurements where one member at a time emits light, and the other members collect light which is measured. It should be noted that the method is not limited to the case of one single member emitting at a time, and all other members collecting, but other measurement regimens are also possible, such as using a sub-set of all members that emit, or a sub-set of all members that collect, or combinations of these.

In the case of member i emitting light, and member i+1 measuring the resulting light fluence, the measured light power may be expressed as $$P_{i,i+1} = P_i K_{i+1} A_i A_{i+1} (4\pi D_i r_{i,i+1})^{-1} \exp(-\mu_{eff(i)} r_{i,i+1}) \quad (3)$$

where $P_i$ is the light power emitted by member i, and $K_{i+1}$ is a conversion factor for the conversion of the fluence rate to power collected by member i+1, and is the distance between member i and i+1. The factor K can be assumed to be the same for all members, or, alternatively, known for each member, or relatively known between all members.

The measurement step provides a set of measurements that in this example can be expressed as:

$$(P_{1,2}$$
$$P_{1,3}$$
$$\ldots$$
$$P_{1,N}$$
$$P_{2,1}$$
$$P_{2,3}$$
$$\ldots$$
$$P_{N,N-1})  \quad (4)$$

In the next step, this dataset may be used to determine the attenuation values $A_i$. When using this dataset with Eq. 3, one obtains a non-linear system of equations with the attenuation values $A_i$, and the optical properties D and $\mu_{eff}$, as unknowns:

$$P_{i,j} = P_i K_j A_i A_j (4\pi D_i r_{i,j})^{-1} \exp(-\mu_{eff(i)} r_{i,j}) \quad (5)$$

This system of equations can be solved using non-linear solution methods, such as, including but not limited to, Newton-type methods, the Levenberg-Marquardt method, or trust-region methods. Note that in general the system of equations may be overdetermined or underdetermined. The optical properties D and $\mu_{eff}$ can either be treated as unknowns, or can be assumed known from prior knowledge.

Equation 5 can be linearised, for example, by taking the logarithm of both sides:

$$\ln(r_{i,j} P_{i,j}) = \ln(A_i) + \ln(A_j) + \ln(P_i K_j (4\pi D_i)^{-1}) - \mu_{eff(i)} r_{i,j} \quad (6)$$

By making the assumptions that $\mu_a \ll \mu_s$ and that $\mu_s$ is known and constant, we get $$\ln(r_{i,j} P_{i,j}) - \ln(P_i K_j (4\pi 3\mu_s)^{-1}) = = \ln(A_i) + \ln(A_j) - \mu_{eff(i)} r_{i,j} \quad (7)$$

Equation 7 represents a system of linear equations with the unknowns $A_i$ and $\mu_{eff(i)}$. This system can be solved by normal methods for solving systems of linear equations, for example the least squares method in cases where the system is under- or overdetermined.

In order to obtain the attenuation values $A_i$, the measurement system must be calibrated to measure the fluence rate in absolute terms. In practise, this condition may be unpractical to achieve. In the case where only relative measurements of fluence rate are available, the values $A_i$ can still be evaluated, but only in relative terms. Relative attenuation values may be used after normalisation. For example, the values $A_i$ may be normalised so that the value of A with the least attenuation is set to 1. This is a conservative approach, since the attenuation will generally be underestimated, so the resulting light doses will also be underestimated. Other normalisation approaches are also possible, for example based on prior knowledge of the normal range of attenuation expected for a particular case.

In other examples, the disclosure may not be limited to the conditions and approximations which are applied in the previous description. In the following, some other examples are described.

In an example, the optical members may not be point sources but distributed sources such as diffusers, for example optical fibres with diffusers. When using diffusers, it may be required to use convolution. The same method could then be used as described above to calculate the effective attenuation coefficient and attenuation values, but it could become more complex. A Finite element method (FEM) may then be applied to solve the complexity. Alternatively, diffusers may be approximated as a plurality of point sources distributed over the dimensions of the diffuser.

In an example, optical members may not be used for light delivery, but instead light sources are positioned directly inside the tissue. The light sources may be photodiodes, e.g., light emitting diodes (LED) or laser diodes.

In an example, optical members may not be used for light collection and detection, but instead light detectors may be positioned directly inside the tissue. The light detectors may be, e.g., photodiodes, photomultiplier tubes, avalanche photodiodes, charge-coupled devices, or CMOS light sensitive devices.

In an example, the medium may not be assumed to have homogeneous optical properties but may instead modelled based on prior knowledge. For example, the medium may be assumed to have regions with different optical properties based on the anatomy of the tissue. The anatomy of the tissue may be known based on imaging data, e.g., x-ray, ultrasound or magnetic resonance imaging. The optical properties may be known for each region in advance based on prior data, or the optical properties may be solved for in the non-linear solver together with the attenuation values.

In an example, the model of the light fluence rate may not be based on the analytical equation but instead numerical methods may be used to solve the transport equation. Examples of such methods are the finite element method, the discrete ordinates method, or Monte Carlo simulations.

In an example, spectral information obtained by spectroscopic measurements, such as multiple wavelengths or white light, may be used to improve the model to further improve the result. By using known absorption spectra of tissue chromophores, e.g., haemoglobin, oxy-haemoglobin, water, and lipids, measurements taken at multiple wavelengths may be used to constrain the model to get accurate results for both the attenuation values and the optical properties.

In an example, the purpose of the method may not only be to determine the attenuation values $A_i$, but also the general optical properties of the tissue, light scattering and light absorption.

In an example, the purpose of the method may not only be to determine the attenuation due to inhomogeneities in the tissue, but also to determine losses in the optical system that performs the measurement. With this approach, the system can be calibrated for light losses in a quick and efficient manner. The light may then be increased to compensate for attenuation of the light, either in the system or the fibres used for transferring light to and from the tissue.

Any method or determinations or calculations described herein may be implemented on a control unit, a data processing device or a computing device. The computer implementation may be done as a computer program or a software to be executed on a control unit, a data processing device or a computing device.

Any methods or determinations or calculations described herein may be performed by a control unit, a data processing device or a computing device. The control unit, data processing device or computing device may be connected to the optical detection system or be a standalone unit.

The control unit, data processing device or a computing device may be implemented by special-purpose software (or firmware) run on one or more general-purpose or special-purpose computing devices. In this context, it is to be understood that each "element" or "means" of such a computing device refers to a conceptual equivalent of a method step; there is not always a one-to-one correspondence between elements/means and particular pieces of hardware or software routines. One piece of hardware sometimes comprises different means/elements. For example, a processing unit serves as one element/means when executing one instruction, but serves as another element/means when executing another instruction. In addition, one element/means may be implemented by one instruction in some cases, but by a plurality of instructions in some other cases. Such a software controlled computing device may include one or more processing units, e.g. a CPU ("Central Processing Unit"), a DSP ("Digital Signal Processor"), an ASIC ("Application-Specific Integrated Circuit"), discrete analog and/or digital components, or some other programmable logical device, such as an FPGA ("Field Programmable Gate Array"). The control unit, data processing device or computing device may further include a system memory and a system bus that couples various system components including the system memory to the processing unit. The system bus may be any of several types of bus structures including a memory bus or memory controller, a peripheral bus, and a local bus using any of a variety of bus architectures. The system memory may include computer storage media in the form of volatile and/or non-volatile memory such as read only memory (ROM), random access memory (RAM) and flash memory. The special-purpose software may be stored in the system memory, or on other removable/non-removable volatile/non-volatile computer storage media which is included in or accessible to the computing device, such as magnetic media, optical media, flash memory cards, digital tape, solid state RAM, solid state ROM, etc. The data processing device may include one or more communication interfaces, such as a serial interface, a parallel interface, a USB interface, a wireless interface, a network adapter, etc., as well as one or more data acquisition devices, such as an A/D converter. The special-purpose software may be provided to the control unit or data processing device on any suitable computer-readable medium, including a record medium and a read-only memory.

In aspect of the disclosure, but not limiting, is a system for determining light attenuation at an optical member inserted in tissue, and/or optical properties, such as light scattering properties and/or light-absorbing properties, of tissue is described. The system may include at least two optical members configured to be inserted into tissue, such as interstitially inserted. The at least two optical members may be configured for emitting and/or collecting light. The system may further include a control unit configured for controlling the at least two optical members so that light is transmitted to the tissue from at least one optical member and light is detected from the tissue by at least one optical member collecting light. This may yield a data set of measured values for pairs of emitting and collecting optical members.

The control unit may be further configured for determining the attenuation values at the optical members and/or the optical properties of the tissue by using the data set of measured values to define a system of equations using a mathematical model of light propagation in tissue. The system of equations may be solved by the control unit by using a numerical solving method.

The system may utilize any of the herein disclosed methods for determining or estimating the attenuation values at the optical members and/or the optical properties of the tissue.

In some examples may the system include a plurality of optical members. In some examples one single member at a time may emit light, and all other members collecting.

Alternatively, in some example other measurement regimens may be possible, such as using a sub-set of all members that emit, or a sub-set of all members that collect, or combinations of these.

In some examples of the system, may the determined attenuation values at the optical members and/or optical properties of the tissue be used for calculating a light dose for photodynamic therapy or laser hyperthermia.

In some examples of the system, may the control unit be configured for using the determined attenuation values at the optical members and/or optical properties of the tissue for light dose delivery for photodynamic therapy or laser hyperthermia.

In some examples of the system, may the optical members be optical fibres, or optical fibres with diffusers. The optical members may transfer emitted light from a light source to the tissue and transfer collected light to a detector. The light source and detector may be any type of light source and detector herein disclosed.

In some examples of the system, may the optical members be photodiodes configured to be arranged in tissue, such as interstitially arranged in tissue.

In some examples of the system, may the optical members be configured to emit light at multiple wavelengths. Further, the control unit may be configured for using spectral detection and known absorption spectra of tissue chromophores to constrain a solution when solving the systems of equations.

In some examples of the system, may the mathematical model of light propagation in tissue be based on Bolzmann transport equation.

In some examples of the system, may the data set of measured values be measured light powers and the mathematical model of light propagation in tissue may be used for expressing measured light power for setting up the system of equations to be solved based on the data set of measured light powers for pairs of emitting and collecting optical members.

In some examples of the system, may the attenuation values at the optical members and the optical properties of the tissue be unknown in the mathematical model of light propagation in tissue.

In some examples of the system, may a Newton-type method, a Levenberg-Marquardt method, or trust-region methods be used as non-linear numerical solving methods for the system of equations.

In some examples of the system, may a least-squares method be used as linear numerical solving method for the linearized system of equations.

In aspect of the disclosure, but not limiting, is a method disclosed for determining light attenuation at an optical member inserted in tissue, and/or optical properties, such as light scattering properties and/or light-absorbing properties, of tissue. The method may include controlling at least two optical members so that light may be transmitted to the tissue from at least one optical member and light may be detected from the tissue by at least one optical member collecting light. This may be used for yielding a data set of measured values for pairs of emitting and collecting optical members. The method may further include determining the attenuation values at the optical members and/or the optical properties of the tissue by using the data set of measured values to define a system of equations using a mathematical model of light propagation in tissue and solving the system of equations by using a numerical solving method.

The mathematical model of light propagation in tissue and a numerical solving method may be any of models or methods herein described.

In some examples may the method include calculating a light dose for photodynamic therapy or laser hyperthermia based on the determined attenuation values at the optical members and/or optical properties of the tissue.

In some examples may the method include controlling a light dose delivery to the photodynamic therapy or laser hyperthermia.

In some examples of the method, may the mathematical model of light propagation in tissue be based on Bolzmann transport equation.

In some examples of the method, may the data set of measured values be measured light powers and the mathematical model of light propagation in tissue may be used for expressing measured light power for setting up the system of equations to be solved based on the data set of measured light power for pairs of emitting and collecting optical members.

In some examples of the method, may a Newton-type methods, a Levenberg-Marquardt method, or trust-region methods be used as non-linear numerical solving methods for the system of equations.

In some examples of the method, may a least-squares method be used as linear numerical solving method for the linearized system of equations.

Any method herein described may be a computer implemented method.

In some aspects of the disclosure is a computer program for determining light attenuation at an optical member inserted in tissue, and/or light scattering properties and light-absorbing properties of tissue described. The computer program may include instructions which, when the computer program is executed by a computer, performs the steps of any of the herein described methods.

EXAMPLES

The method in the disclosure was applied to measurement data obtained from a system for PDT of prostate tissue, the SpectraCure P18 system with IDOSE, J. Swartling, et al "System for interstitial photodynamic therapy with online dosimetry—First clinical experiences of prostate cancer", J Biomed Opt. 15, 058003 (2010). The system uses 18 individual optical members that can be used with for therapeutic PDT light delivery, or for optical spectroscopic measurements of the tissue for the purpose of dose planning.

In order to obtain the attenuation values, the system was calibrated so that the conversion factor K was known for each optical member. This was done by subjecting each member in light-collecting mode to a known light fluence (W/cm2) in a reference tissue phantom, and registering the corresponding reading on the internal spectrometer.

Measurement data was acquired by inserting the optical members into a tissue phantom (mix of water, intralipid and ink) with scattering and absorption properties similar to tissue at the measurement wavelength, 690 nm. Measurements were performed by the system by cycling through all combinations of emitting and collecting member, yielding a set a of measurements $$(P_{1,2}$$
$$P_{1,3}$$
$$...$$
$$P_{1,18}$$
$$P_{2,1}$$
$$P_{2,3}$$
$$...$$
$$P_{18,17}) \quad (5)$$

This data set was then subjected to the evaluation of attenuation values and optical properties. To demonstrate the improvement given by the new evaluation method, the corresponding results using the old model were calculated for comparison. In the old model, the optical property $\mu_{eff}$ was simply determined as the slope of log(P) around each member as a function of r (the logarithm of eq. 3). The attenuation values were then estimated based on the deviation from the least-squares solution to the $\mu_{eff}$ value for the measurement data.

The actual value of $\mu_{eff}$ was independently measured using time-of-flight spectroscopy for reference.

Figure 2:
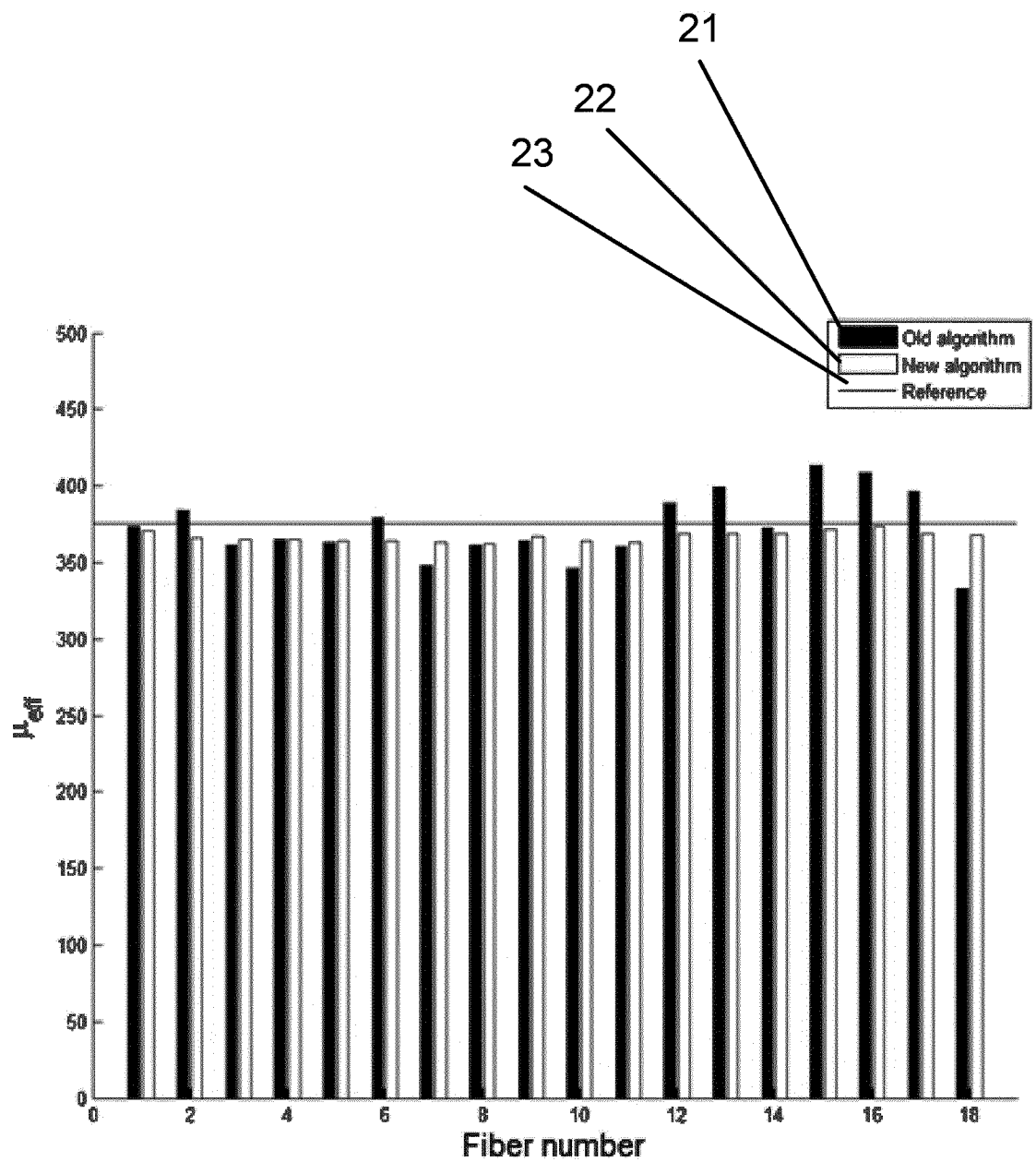
FIG. 2 is illustrating evaluated optical properties ($\mu^{eff}$) using the old evaluation method (21) and the new, disclosed method (22), in a homogeneous tissue phantom. The value of $\mu_{eff}$ as measured by an independent reference measurement method is also shown (23).

FIG. 2 shows $\mu_{eff}$ values for each emitter member, using the old method and the new method. The value obtained by the reference measurement is also shown. Since the tissue phantom is homogeneous, the results for each member should be the same. Clearly, the results are much improved by the new method compared with the old.

Figure 3:
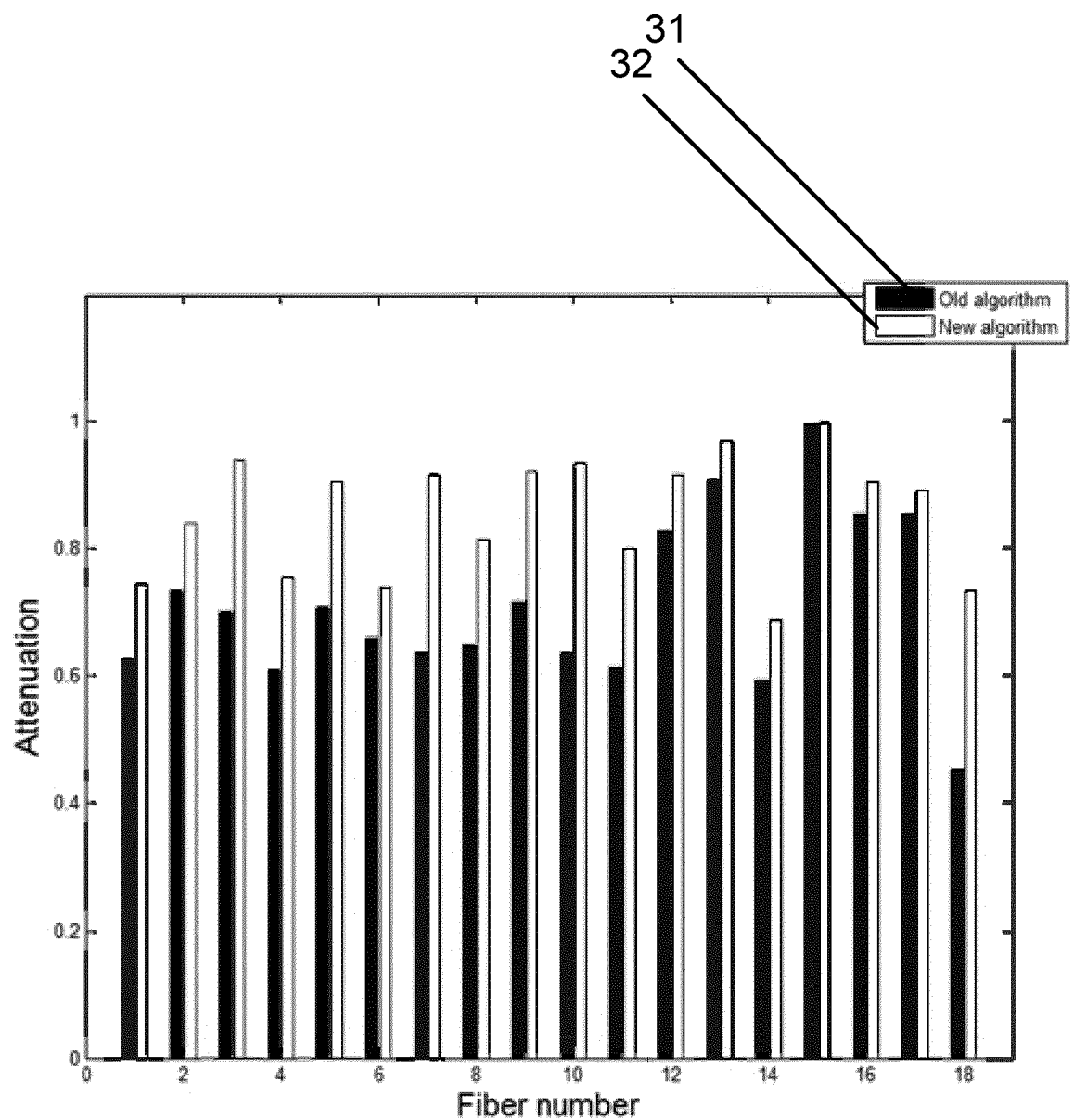
FIG. 3 is illustrating evaluated attenuation values using the old evaluation method (31) and the new, disclosed method (32), in the same homogeneous tissue phantom as used in FIG. 2.

FIG. 3 shows the attenuation values for each emitter member, using the old method and the new method. In this case, there are no reference values for the actual attenuation values, which are caused by losses in the optical member line from the phantom to the detection system. However, it is clear that with the old method, part of these attenuation losses will translate to errors in the evaluation of $\mu_{eff}$, so it cannot be expected that the evaluated attenuation values are correct with the old method.

In another example, the algorithm was applied to actual measurements taken of prostate tissue in vivo in a clinical situation. The measurements were taken in the same manner as described in J. Swartling, et al "System for interstitial photodynamic therapy with online dosimetry—First clinical experiences of prostate cancer", J Biomed Opt. 15, 058003 (2010). The data set was again based on 18 optical members.

Figure 4:
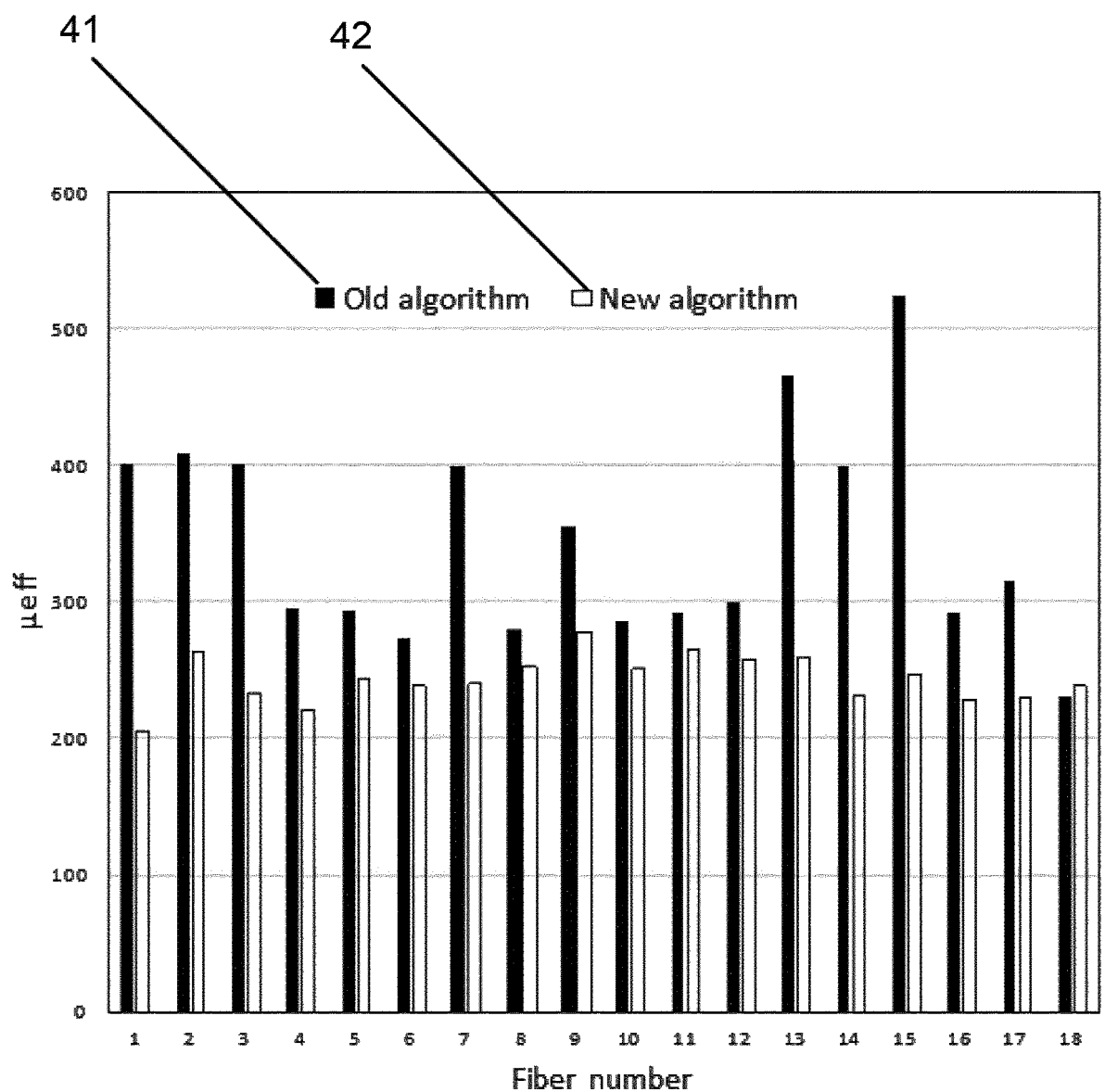
FIG. 4 is illustrating evaluated optical properties ($\mu_{eff}$) using the old evaluation method (41) and the new, disclosed method (42) for prostate tissue.

FIG. 4 shows $\mu_{eff}$ values for prostate tissue for each emitter member, using the old method and the new method. The old algorithm shows much more variation in the obtained values than the new algorithm. The values obtained by the old algorithm are also generally higher than those obtained with the new algorithm.

Figure 5:
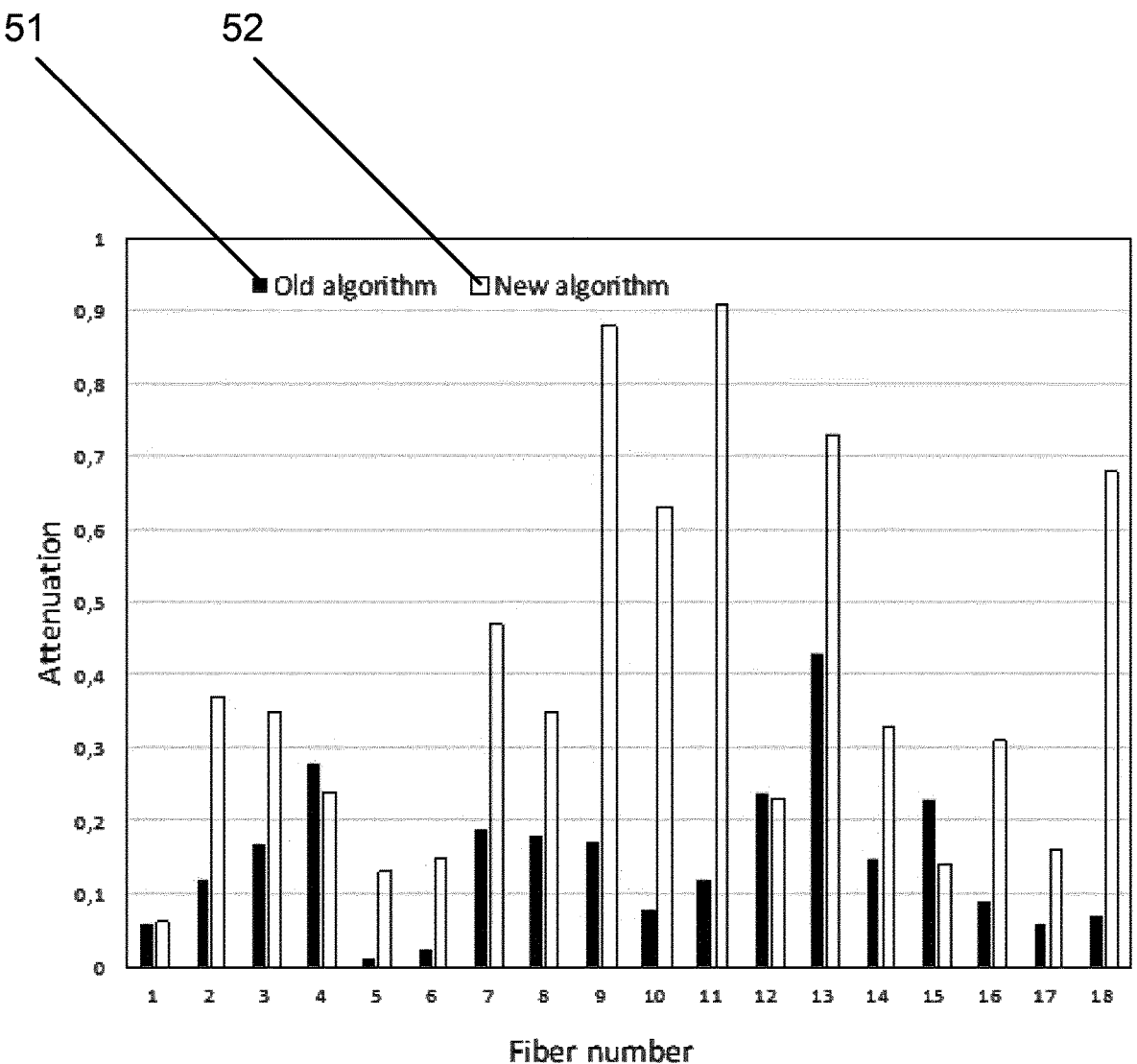
FIG. 5 is illustrating evaluated attenuation values using the old evaluation method (51) and the new, disclosed method (52), in the same prostate tissue as used in FIG. 4.

FIG. 5 shows the attenuation values in the prostate for each emitter member, using the old method and the new method. In this example, the attenuation values are generally lower than in the homogeneous phantom example, which is expected since there will be bleeding in the prostate tissue that causes increased attenuation.

The present invention has been described above with reference to specific examples. However, other examples than the above described are equally possible within the scope of the disclosure. Different method steps than those described above, performing the method by hardware or software, may be provided within the scope of the invention. The different features and steps of the invention may be combined in other combinations than those described. The scope of the disclosure is only limited by the appended patent claims.

The indefinite articles "a" and "an," as used herein in the specification and in the claims, unless clearly indicated to the contrary, should be understood to mean "at least one." The phrase "and/or," as used herein in the specification and in the claims, should be understood to mean "either or both" of the elements so conjoined, i.e., elements that are conjunctively present in some cases and disjunctively present in other cases.

The invention claimed is:

1. A system for determining light attenuation values at an optical member inserted in tissue and/or losses in an optical measuring system, the system comprising:
   at least two optical members configured to be inserted into tissue, said at least two optical members are configured for emitting and/or collecting light;
   a control unit configured for:
      controlling said at least two optical members so that light is transmitted to said tissue from at least one of said optical members and light is detected from said tissue by at least one of said optical members collecting light, thereby yielding a data set of measured values for pairs of emitting and collecting optical members;
      wherein said control unit is further configured for determining said light attenuation values;
      determining light-attenuating inhomogeneities at said optical member and/or losses in said optical measuring system using said light attenuation values, wherein said light attenuation values are determined using said data set of measured values to define a system of equations using a mathematical model of light propagation in tissue; and
      solving said system of equations by using a numerical solving method.

2. The system of claim 1, wherein said light attenuation values correspond to light attenuation in the tissue close to said optical member or in said optical member.

3. The system of claim 1, wherein said determined attenuation values at said optical members is used for calculating a light dose for photodynamic therapy or laser hyperthermia.

4. The system of any claim 1, wherein the control unit is configured for using said determined attenuation values at said optical members when determining light dose delivery for photodynamic therapy or laser hyperthermia.

5. The system of any claim 1, wherein said optical members are:
   optical fibers, or optical fibers with diffusers, configured to transfer emitted light from a light source to said tissue and to transfer collected light to a detector; or
   photodiodes configured to be arranged in tissue.

6. The system of claim 1, wherein said optical members are configured to emit light at multiple wavelengths and wherein said control unit is configured for using spectral detection and known absorption spectra of tissue chromophores to constrain a solution when solving said systems of equations.

7. The system of claim 1, wherein said mathematical model of light propagation in tissue is based on a Boltzmann transport equation.

8. The system of claim 1, wherein said data set of measured values are measured light powers and said mathematical model of light propagation in tissue is used for expressing measured light power for setting up said system of equations to be solved based on said data set of measured light powers for said pairs of emitting and collecting optical members.

9. The system of claim 1, wherein said attenuation values at said optical members and optical properties of said tissue are unknown in said mathematical model of light propagation in tissue.

10. The system of claim 1, wherein said system of equations is solved by a non-linear numerical solving method.

11. The system of claim 1, wherein said system of equations is a linearized system of equations solved by a method for solving linear equations.

12. A computer program for determining light attenuation values caused by light-attenuating inhomogeneities at an optical member inserted in tissue and/or losses in an optical measuring system, the computer program comprising instructions which, when executed by a computer, cause the computer program to:
   control at least two optical members so that light is transmitted to said tissue from at least one optical member and light is detected from said tissue by at least one optical member collecting light, thereby yielding a data set of measured values for pairs of emitting and collecting optical members;
   determine said light attenuation values;
   determine light-attenuating inhomogeneities at said optical member and/or losses in an optical measuring system using said light attenuation values, wherein said light attenuation values are determined using said data set of measured values to define a system of equations using a mathematical model of light propagation in tissue; and
   solve said system of equations by using a numerical solving method.

13. The computer program of claim 12, wherein said instructions, when executed by said computer, further cause said computer program to:
   calculate a light dose for photodynamic therapy or laser hyperthermia by including said determined attenuation values at said optical members; and
   control a light dose delivery to said photodynamic therapy or laser hyperthermia.

14. The computer program of claim 12, wherein said mathematical model of light propagation in tissue is based on a Boltzmann transport equation.

15. The computer program of claim 12, wherein said data set of measured values are measured light powers and said mathematical model of light propagation in tissue is used for expressing measured light power for setting up said system of equations to be solved based on said data set of measured light powers for said pairs of emitting and collecting optical members.

16. The computer program of claim 12, wherein;
   said system of equation is non-linear and said numerical solving method comprises a non-linear numerical solving method; or
   said system of equations is a linearized system of equations and said numerical solving method comprises a method for solving linear equations.

* * * * *